United States Patent
Holman et al.

(10) Patent No.: US 6,953,470 B2
(45) Date of Patent: Oct. 11, 2005

(54) CATHETER SUPPORT

(75) Inventors: Thomas J. Holman, Minneapolis, MN (US); Richard Dunn, Brooklyn Park, MN (US); Jan Seppala, Maple Grove, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 524 days.

(21) Appl. No.: 10/241,138

(22) Filed: Sep. 11, 2002

(65) Prior Publication Data

US 2004/0049153 A1 Mar. 11, 2004

(51) Int. Cl.[7] .............................................. A61M 29/00
(52) U.S. Cl. ........................ 606/194; 604/915; 604/921; 604/103
(58) Field of Search .............................. 604/96.01, 103, 604/103.04, 103.09, 915, 917, 921, 523–524, 533–535; 606/192, 194

(56) References Cited

U.S. PATENT DOCUMENTS

| | | | |
|---|---|---|---|
| 4,702,252 A | * 10/1987 | Brooks et al. ............... | 606/195 |
| 5,378,237 A | * 1/1995 | Boussignac et al. ...... | 604/103.1 |
| 5,425,712 A | 6/1995 | Goodin ......................... | 604/96 |
| 5,549,552 A | * 8/1996 | Peters et al. .............. | 604/103.1 |
| 5,676,654 A | 10/1997 | Ellis et al. ................... | 604/103 |
| 5,716,373 A | 2/1998 | Wolvek et al. ............... | 606/194 |
| 5,779,731 A | 7/1998 | Leavitt ......................... | 606/194 |
| 6,048,338 A | 4/2000 | Larson et al. ................ | 604/523 |
| 6,270,504 B1 | * 8/2001 | Lorentzen Cornelius et al. ........................... | 606/108 |
| 6,436,090 B1 | * 8/2002 | Sanchez et al. ............. | 604/525 |

\* cited by examiner

*Primary Examiner*—LoAn H. Thanh
(74) *Attorney, Agent, or Firm*—Vidas, Arrett, Steinkraus

(57) ABSTRACT

A balloon catheter comprises a balloon, an inner shaft, an outer shaft and a transition shaft. The transition shaft has a proximal portion and a distal portion joined by a tapered portion. The proximal portion has a diameter greater than the distal portion. The proximal portion has a first end portion engaged to at least a portion of the outer shaft at a first engagement site. At least a portion of the proximal waist is engaged to the proximal portion of the transition shaft at a second engagement site. At least a portion of the end region of the inner shaft is engaged to the distal portion of the transition shaft at a third engagement site. The distal portion extends through the balloon wherein at least a portion of the distal waist of the balloon is engaged to the distal portion of the transition shaft at a forth engagement site.

9 Claims, 5 Drawing Sheets

CATHETER SUPPORT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

Embodiments of this invention are directed to the field of intravascular medical devices, and more particularly to the field of catheters such as angioplasty, neurological and guide catheters, among others, which may be used in various medical procedures such as percutaneous transluminal angioplasty (PTA), percutaneous transluminal coronary angioplasty (PTCA) as well as in procedures involving the placement of medicines and medical devices within the body.

Some embodiments of the invention are directed to all forms of catheters which may be advanced through a body lumen or vessel. Some examples of catheters are over-the-wire (OTW) catheters, such as are described in U.S. Pat. No. 5,047,045; single-operator-exchange (SOE) balloon catheters, such as are described in U.S. Pat. Nos. 5,156,594 and 5,549,552. Other examples of catheters which may incorporate the unique features of the present invention may include rapid-exchange catheters, guide catheters, etc.

2. Description of the Related Art

Intravascular diseases are commonly treated by relatively non-invasive techniques such as PTA and PTCA. These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened. In other uses a catheter may be used to delivery an endoprosthesis such as a stent, graft, stent-graft, vena cava filter or other implantable device or devices herein after collectively referred to as a stent or stents. Where a stent is to be delivered into a body lumen the catheter may include one or more inflatable portions or balloons. Typically, the stent is retained in the predelivery state about the catheter shaft, or a portion thereof such as a balloon, by crimping and/or through the use of a retaining mechanism such as sleeve, sheath or sock.

Balloons and balloon catheters may be particularly useful for the delivery of expandable, implantable medical devices such as stents, grafts, stent-grafts, vena cava filters, hereinafter referred to cumulatively as stents. Stents and catheters used in their delivery are commonly used and as such their structure and function are well known.

A stent is a generally cylindrical prosthesis introduced via a catheter into a lumen of a body vessel in a configuration having a generally reduced diameter and then expanded. In its expanded configuration, the stent supports and reinforces the vessel walls while maintaining the vessel in an open, unobstructed condition.

In order to properly position a stent and/or balloon within a body lumen, the catheter must be advanced through the narrow confines of the body. Typically the balloon and/or stent is located near the distal end of the catheter. In order to advance the distal end of most prior catheters further in to a body lumen, the inner shaft or catheter member is utilized to transmit force to the distal end. However, the inner is typically soft and flexible which often results in poor transmission of push.

The present invention, in accordance with the various embodiments presented herein, addresses the shortcoming of poor push transmission common to many catheters.

Without limiting the scope of the invention, a brief summary of various embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

The entire content of all of patents or other references listed within the present patent application are incorporated herein by reference.

BRIEF SUMMARY OF THE INVENTION

The present invention is directed to several embodiments. In at least one embodiment the invention is directed to elongate medical devices such as balloon catheters which include a novel a transitional shaft portion that engages the inner shaft as well as the outer shaft of the catheter. The balloon is disposed about the transitional shaft by engaging the proximal waist and distal waist of the balloon to the shaft.

In at least one embodiment the transitional shaft comprises a proximal region having a first diameter sized to engage the outer shaft of the catheter. The transition shaft further comprises a transition point wherein the shaft tapers radially inward to provide a distal region having a second diameter suitable for engagement to the inner shaft and/or the distal waist of the balloon.

In some embodiments the transition shaft defines an extension of the inflation lumen defined by the outer shaft. The transition shaft includes one or more inflation holes or pores to allow inflation fluid to be passed through the inflation lumen and into the balloon interior for expansion thereof.

In some embodiments the transitional shaft is characterized as being an extension of the distal outer catheter shaft.

In some embodiments at least a portion of the transitional shaft is constructed of a material having different flexibility characteristics than at least one of the inner shaft and outer shaft.

In some embodiments, at least a portion of the transition shaft is characterized as having greater columnar strength than the inner or outer shaft. In some embodiments, at least a portion of the transition shaft is characterized as having a pattern grooves which comprise one or more: slots, spirals, stripes or other features. The pattern of groves provides the transition shaft with desired flexibility characteristics without compromising push.

In at least one embodiment at least a portion of the transitional shaft is characterized as being more rigid than at least one of the inner shaft and outer shaft.

Additional details and/or embodiments of the invention are provided below.

BRIEF DESCRIPTION OF THE SEVERAL VIEWS OF THE DRAWINGS

A detailed description of the invention is hereafter described with specific reference being made to the following drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
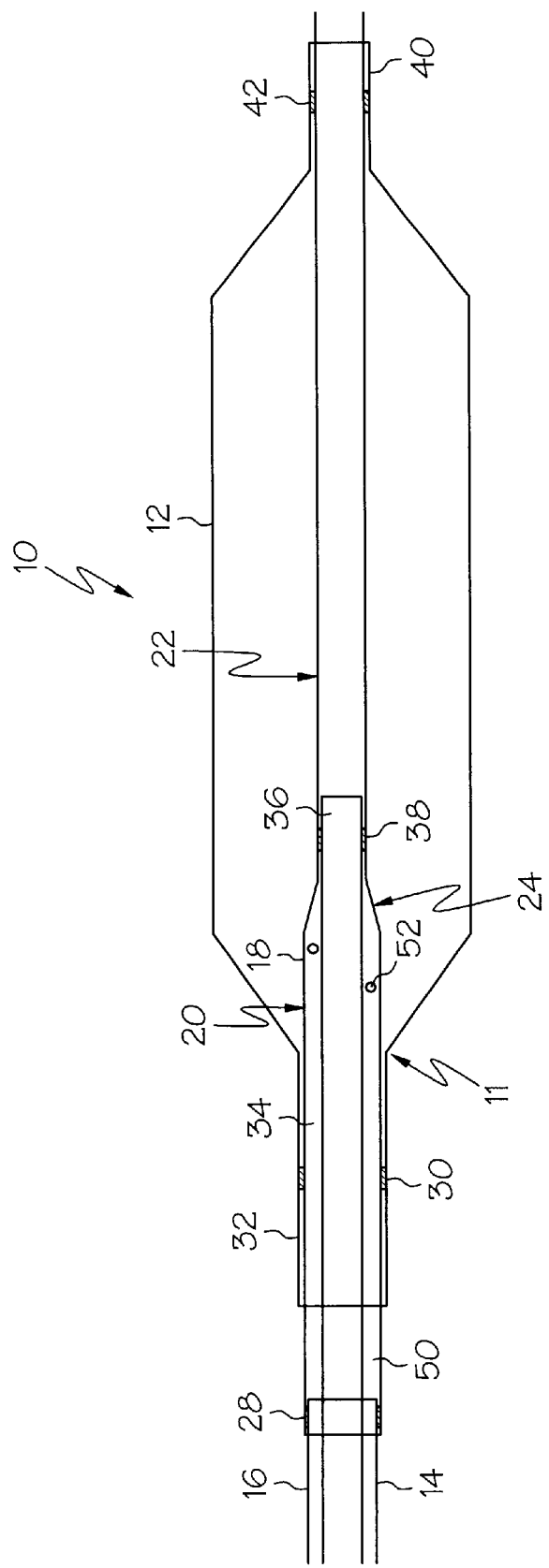
FIG. 1 is a cross-sectional side view of an embodiment of the invention.

As previously discussed above, the present invention is directed to a variety of embodiments. For example, embodiments of the invention are depicted in FIG. 1, wherein a catheter, indicated generally at 10, is shown. The distal region 11 of catheter 10, is equipped with a balloon 12 that is expandable from a first expanded state to one or more expanded states. In FIG. 1 the balloon 12 is shown in an expanded state, such as the balloon would be placed in for dilatation of a vessel or delivery of a medical device such as a stent.

Catheter 10 comprises an inner shaft 14 as well as an outer shaft 16 disposed thereabout. In addition to shafts 14 and 16, the embodiment of FIG. 1 further comprises a transition shaft 18. Transition shaft 18 provides the catheter 10 with a unique means for engaging balloon 12, inner shaft 14 and outer shaft 16 together. The resulting combination of components allows push force to be transmitted to the distal region 11 of the catheter 10, even if the inner shaft 14 is constructed of an extremely flexible material. As a result of improved push transmission, control, placement and trackability of the distal region 11 is improved.

The transition shaft 18 is comprised of a proximal portion 20 and a distal portion 22. As is shown in the embodiment of FIG. 1 the proximal portion 20 may have a diameter greater than that of the distal portion 22. The proximal portion 20 is joined to the distal portion 22 at transition or tapered portion 24. In at least one embodiment the proximal portion 22 has a greater columnar strength than one or more of the distal portion 22, the inner shaft 14, and/or outer shaft 16.

The transition shaft 18 may be engaged to the balloon 12, inner shaft 14 and outer shaft 16 respectively in a variety of different manners and configurations. In the embodiment shown in FIG. 1, the proximal portion 20 of transition shaft 18 is engaged to the outer shaft 16 at a first engagement site 28. In the embodiment shown, the proximal portion 20 of transition shaft 18 is disposed about the outer shaft 16, however it should be noted that other configurations are possible. For example, if desired, the outer shaft 16 may have a diameter sufficient to allow the proximal portion 20 of transition shaft 18 to be inserted into the outer shaft 18 for engagement thereto. Other engagement possibilities, including end-to-end engagement (i.e. butt-welding), may also be used.

Moving distally from the first engagement site 28, it is shown that the proximal waist 32 of the balloon 12 is disposed about the proximal portion 20 of transition shaft 18. At least a portion of the proximal waist 32 of balloon 12 is engaged to the proximal portion 20 of transition shaft 18 at a second engagement site 30.

As is clear from the embodiment shown in FIG. 1, the inner shaft 14 extends distally from the outer shaft 16 and into the lumen or space 34 defined by the transition shaft 18. However, at a point distal to the tapered portion 24 of the transition shaft 18, the inner shaft 14 ends at end region 36. At least a portion of the end region 36 of the inner shaft 14 is engaged to the distal portion 22 of the transition shaft 18 at a third engagement site 38.

The distal portion 22 of transition shaft 18 extends distally through balloon 12. The distal waist 40 of balloon 12 is engaged at a forth engagement site 42 to a portion of the transition shaft 18 thereunder.

The various engagement sites 28, 30, 38 and 42 are points or areas where the respective portions of the transition shaft 18 are bonded, welded or otherwise engaged to the various components described above. In at least one embodiment, the engagement sites are provided by laser welding methods and techniques. Examples of suitable laser welding methods are described in copending application Ser. No. 10/131798, entitled Selective Manipulation of Material for Medical Devices and Methods and Devices, filed Apr. 24, 2002, the entire content of which being incorporated herein by reference.

Other engagement techniques may include frictional engagement, chemical bonding or welding, and/or adhesive bonding of the respective components.

In the embodiment shown in FIG. 1, the various engagement sites 28, 30, 38 and 42 are depicted as blocks joining the respective components. It should be understood however, that such a depiction of the catheter 12 is merely a convenient format to illustrate the manner of assembly of the various components of the catheter 12. While in some cases, particularly where the engagement site comprises an adhesive placed between the components, the components may in fact be separated to some extent. One of ordinary skill however, will recognize that in the case where an engagement site comprises a weld, the respective components would be melted together, and thereby joined, at the engagement site. For example, in the case of third engagement site 38, the inner shaft 14 is depicted as underlaying the distal portion 22 of transition shaft 18. Where engagement site 38 comprises a weld, the inner shaft 14 is fuzed to the transition shaft 18 as a result of temporarily melting the components and allowing them to subsequently cool at the engagement site 38.

As is shown in FIG. 1, an additional feature of the transition shaft 18 is that the shaft 18 effectively extends the inflation lumen 50 defined by the outer shaft 16. The lumen 34 defined by the transition shaft 18 is in fluid communication with the inflation lumen 50, thereby effectively extending the inflation lumen 50 into the balloon 12. Inflation fluid is able to enter the interior of the balloon 12 via inflation holes or ducts 52 through the transition shaft 18. In the embodiment shown, inflation ducts 52 are located on the proximal portion 20 of the transition shaft 18 and are positioned proximal to the tapered portion 24. In alternative embodiments however, the ducts 52 are positioned within the tapered portion 24 and/or in the distal portion 22, proximal to the third engagement site 38.

Figure 2:
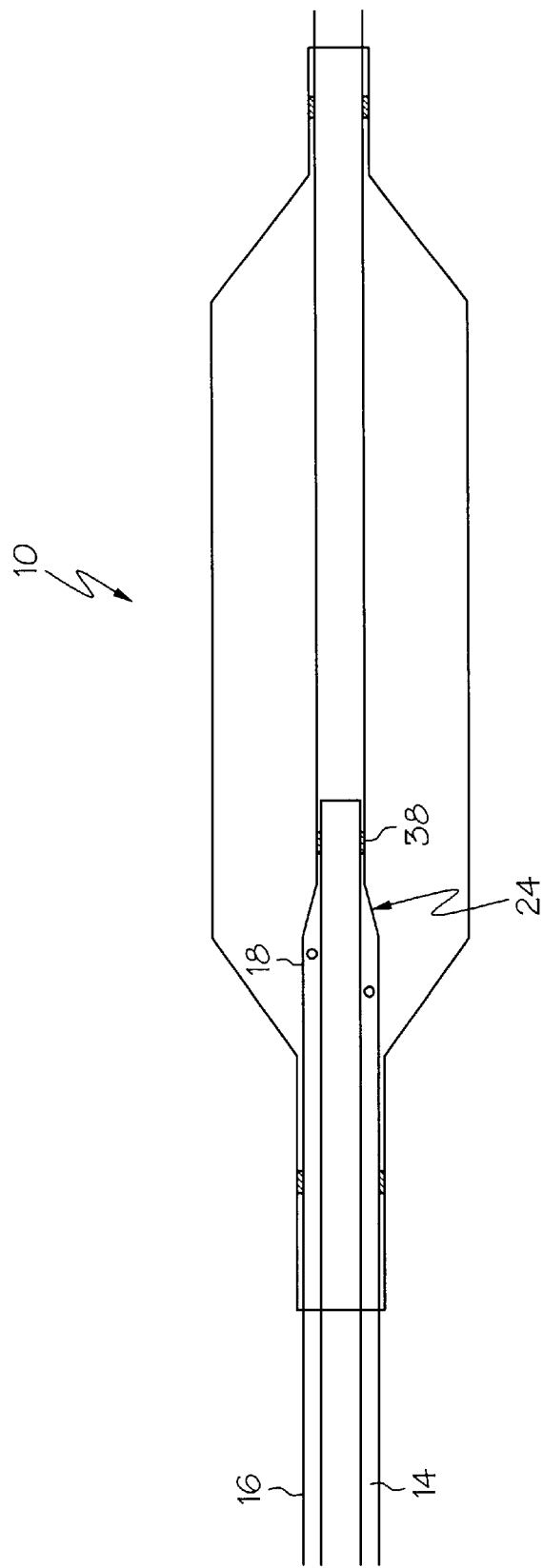
FIG. 2 is a cross-sectional side view of an embodiment of the invention.

In an alternative embodiment shown in FIG. 2, the transition shaft 18 is a distal extension of the outer shaft 16.

In the embodiment shown the transition or tapered portion 24 is effectively a necked down region of the outer shaft 16 which provides a diameter sufficiently reduced to be engaged to the inner shaft 14 at the third engagement site 38.

Figure 3:
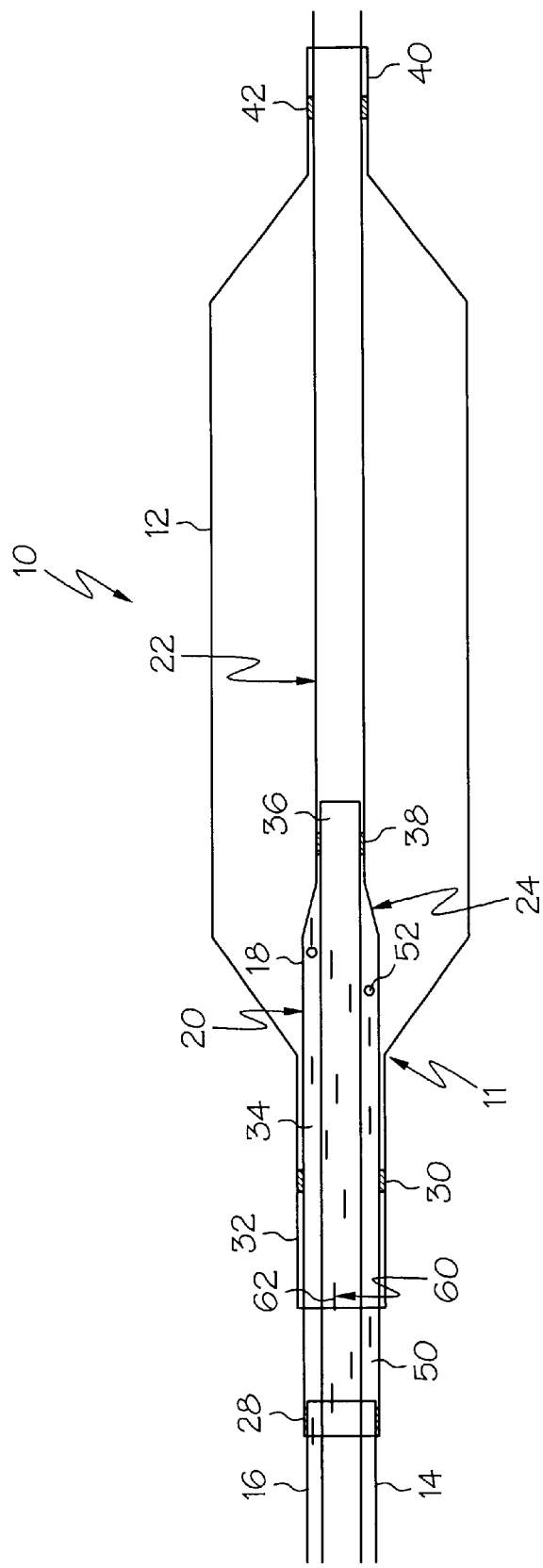
FIG. 3 is a cross-sectional side view of an embodiment of the invention wherein the transition shaft includes a pattern grooved slots.
Figure 4:
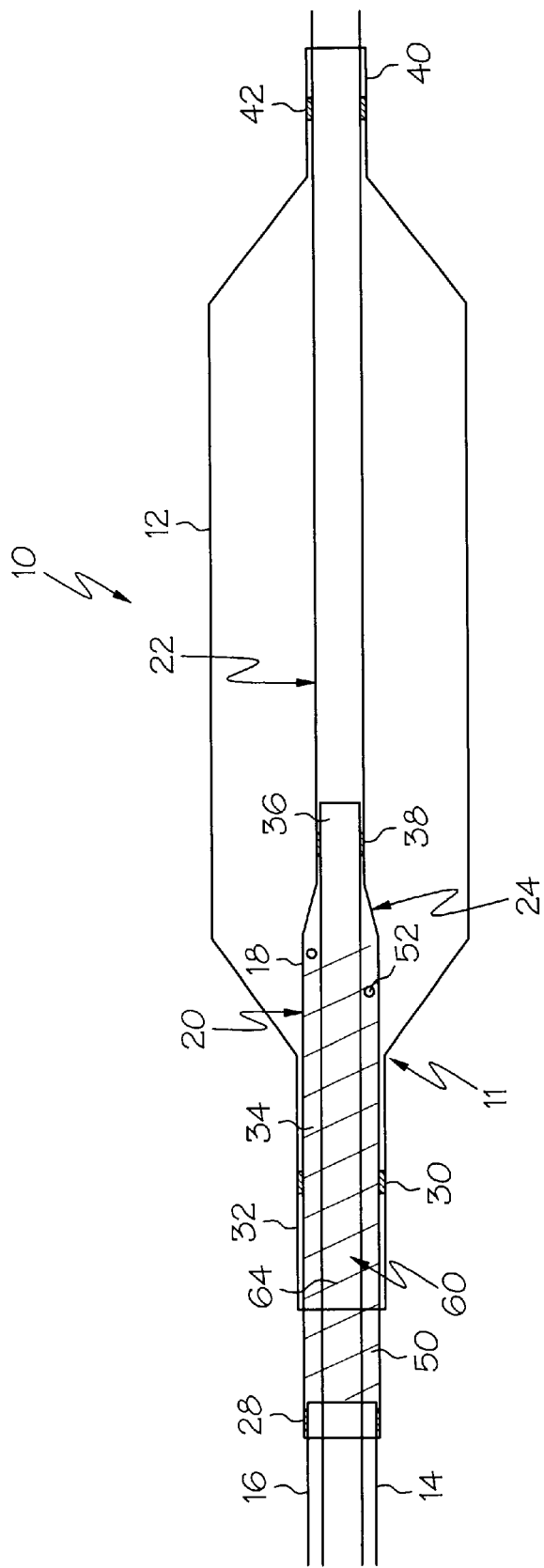
FIG. 4 is a cross-sectional side view of an embodiment of the invention wherein the transition shaft includes a grooved spiral.
Figure 5:
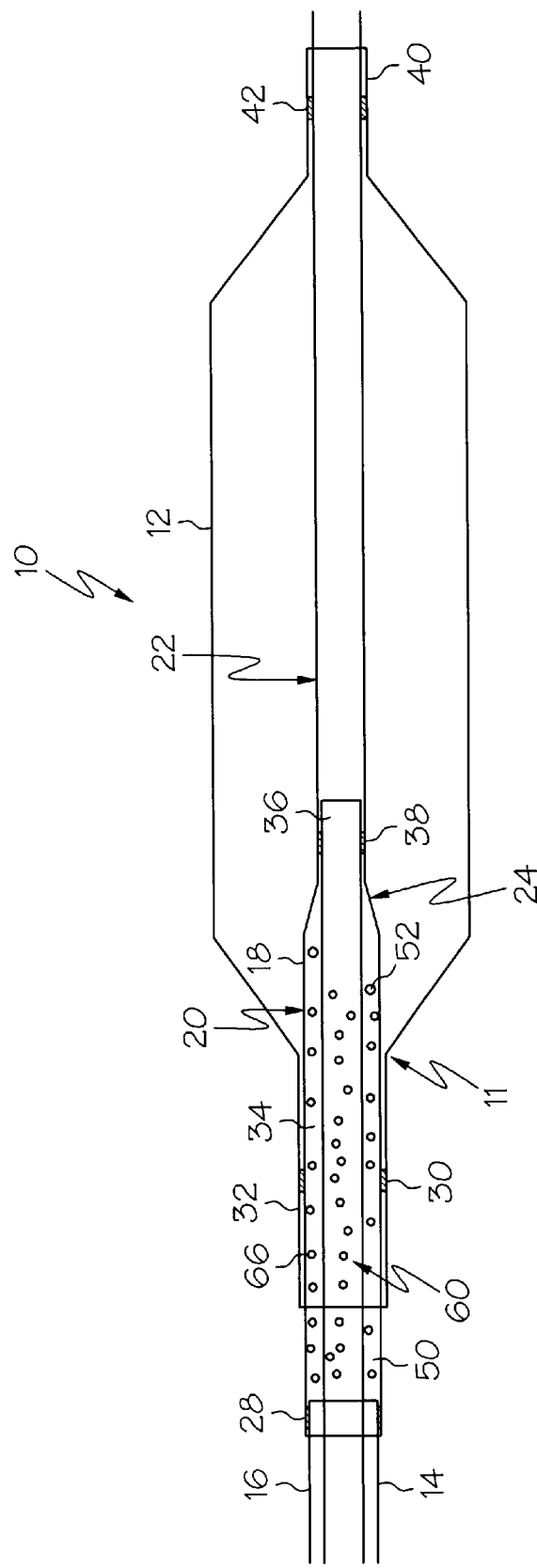
FIG. 5 is a cross-sectional side view of an embodiment of the invention wherein at least a portion of the transition shaft is porous.

In other embodiments of the invention, such as are shown in FIGS. 3–5 the proximal portion 20 of the transition shaft 18 includes a pattern of indentations or grooves 60. Where the proximal portion 20 is provided with improved columnar strength relative to the distal portion 22 or other shafts 14 and 16, the pattern of grooves 60 allows the proximal portion to have improved flexibility without compromising the improved columnar strength. The pattern 60 may have a variety of configurations. For example: in FIG. 3, the pattern of grooves 60 comprise a plurality of slots or notches 62, in FIG. 4 the pattern 60 is comprised of one or more spiral 64; and in FIG. 5 the pattern 60 comprises a plurality of indentations or pores 66. Pores 66 may or may not extend through the transition shaft 18. Where the pores do extend through the shaft 18, the pores may act to supplement or replace the inflation function of ducts 52. Other patterns 60 may also be provided in order to provide any degree of desired flexibility and/or columnar strength.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A balloon catheter comprising:
    a medical balloon expandable from an uninflated state to at least one inflated state, the medical balloon having a proximal waist and a distal waist;
    an inner shaft, the inner shaft extending into the medical balloon, the inner shaft defining an end region within the medical balloon;
    an outer shaft disposed about at least a portion of the inner shaft;
    a transition shaft, the transition shaft having a proximal portion and a distal portion, the proximal portion having a diameter greater than that of the distal portion, the proximal portion and the distal portion being joined by a tapered portion, the proximal portion having a first end portion engaged to at least a portion of the outer shaft at a first engagement site, at least a portion of the proximal waist being engaged to the proximal portion of the transition shaft at a second engagement site, at least a portion of the end region of the inner shaft being engaged to the distal portion of the transition shaft at a third engagement site, the distal portion extending through the medical balloon wherein at least a portion of the distal waist of the balloon is engaged to the distal portion of the transition shaft at a forth engagement site.

2. The balloon catheter of claim 1 wherein the outer shaft and at least the proximal portion of the transition shaft define an inflation lumen, the inflation lumen.

3. The balloon catheter of claim 2 wherein the transition shaft further comprises at least one inflation duct in fluid communication with the inflation lumen and the medical balloon.

4. The balloon catheter of claim 1 wherein at least one of the first engagement site, second engagement site, third engagement site and forth engagement site are formed according to at least one technique selected from the group consisting of: applying a chemical adhesive, chemical bonding, chemical welding, heat welding, laser welding, frictional engagement and any combination thereof.

5. The balloon catheter of claim 1 wherein at least a portion of the inner shaft is characterized as being more flexible than at least one of the outer shaft and transition shaft.

6. The balloon catheter of claim 1 wherein at least a portion of the transition shaft has a greater columnar strength than at least one of the inner shaft and outer shaft.

7. The balloon catheter of claim 1 wherein at least a portion of the proximal portion of the transition shaft has a greater columnar strength than at least one of the distal portion of the transition shaft, inner shaft and outer shaft.

8. The balloon catheter of claim 1 wherein at least a portion of the proximal portion of the transition shaft comprises a predetermined pattern of grooves.

9. The balloon catheter of claim 8 wherein the predetermined pattern of grooves is selected from at least one member of the group consisting of: slots, spirals, pores and any combination thereof.

\* \* \* \* \*